(12) United States Patent
Chu

(10) Patent No.: US 7,390,298 B2
(45) Date of Patent: Jun. 24, 2008

(54) EXPANDABLE SURGICAL RETRACTOR FOR INTERNAL BODY SPACES APPROACHED WITH MINIMALLY INVASIVE INCISIONS OR THROUGH EXISTING ORIFICES

(75) Inventor: David Z. J. Chu, S. Pasadena, CA (US)

(73) Assignee: City of Hope, Duarte, CA (US)

( * ) Notice: Subject to any disclaimer, the term of this patent is extended or adjusted under 35 U.S.C. 154(b) by 315 days.

(21) Appl. No.: 10/749,877

(22) Filed: Dec. 31, 2003

(65) Prior Publication Data

US 2004/0236186 A1 Nov. 25, 2004

Related U.S. Application Data

(60) Provisional application No. 60/438,168, filed on Jan. 6, 2003.

(51) Int. Cl.
*A61B 1/32* (2006.01)
*A61M 29/00* (2006.01)

(52) U.S. Cl. .................. 600/209; 600/201; 606/198; 604/105

(58) Field of Classification Search .......... 600/201, 600/209, 206, 216, 219; 606/198, 200; 604/105, 604/106, 107
See application file for complete search history.

(56) References Cited

U.S. PATENT DOCUMENTS

| | | | | |
|---|---|---|---|---|
| 1,155,169 A | * | 9/1915 | Starkweather | ............... 604/105 |
| 3,192,928 A | * | 7/1965 | Horton | ....................... 606/191 |
| 5,201,756 A | * | 4/1993 | Horzewski et al. | .......... 606/198 |
| 5,558,665 A | | 9/1996 | Kieturakis | |
| 5,730,726 A | * | 3/1998 | Klingenstein | ............... 604/105 |
| 5,888,196 A | | 3/1999 | Bonutti | |
| 5,976,079 A | * | 11/1999 | Volz et al. | .................... 600/209 |
| 6,280,414 B1 | * | 8/2001 | Shah et al. | .................. 604/104 |
| 2001/0000799 A1 | * | 5/2001 | Wessman et al. | ............ 606/200 |
| 2003/0095781 A1 | * | 5/2003 | Williams | .................... 385/146 |

\* cited by examiner

*Primary Examiner*—Cary E. O'Connor
(74) *Attorney, Agent, or Firm*—Michael J. Wise; Perkins Coie LLP

(57) ABSTRACT

An expandable surgical retractor for use in minimal incision surgery is disclosed. The retractor consists of a fiber optic central rod surrounded by flexible wires designed to create an open space for visualization and surgical work within an illuminated surgical field. The flexible wires are disposed via selective pressure of the surgeon and are variable in number. The configuration will allow for both forward and back illumination of the surgical field. The expandable surgical retractor allows for surgical visualization in anatomical areas heretofore too complicated for surgical consideration. Other embodiments of the expandable surgical retractor are contemplated wherein a handle with an aperture may replace the central rod. The flexible wires may fit in openings around the aperture. The handle, in this embodiment, may have a light source and may be adapted to be used in select areas of anatomy. Further, the handle may be transparent.

51 Claims, 4 Drawing Sheets

EXPANDABLE SURGICAL RETRACTOR FOR INTERNAL BODY SPACES APPROACHED WITH MINIMALLY INVASIVE INCISIONS OR THROUGH EXISTING ORIFICES

PRIORITY CLAIM

This application claims priority to U.S. Provisional Patent Application No. 60/438,168 filed Jan. 6, 2003, which is incorporated herein in its entirety by reference.

BACKGROUND OF THE INVENTION

Surgery is an art in which the final result has been based on a series of calculated steps. Initially, the proper diagnosis and pre-operative considerations must be confirmed. Among a multitude of important considerations are the choice of procedure, post-operative conditions and possible complications. All variables must be weighed for and against the risk to the patient and the favorable prognosis given the surgery planned. Intra-operative considerations are often times routine and may be made so by appropriate pre-operative preparation and intra-operative skill of the surgeon and surgical team. To a great measure, the surgeon's success is dependent on the ability to accurately visualize the surgical site. Knowledge of anatomy, choice of surgical approach, or location of incision, and dissection are key to this visualization.

Medical and surgical advances have greatly increased the surgeon's ability to address pathologies of the body that were once beyond a reasonable approach. For example, the reattachment of a limb would be impossible were it not for microsurgical technique and visualization. Additionally, procedures once reserved for "open" surgical approaches have now been replaced by minimal incision approaches. In fact, minimal incision procedures are fast becoming the standard surgery of choice for many procedures. Advances in surgical-scopy technique, or surgical scope procedures, and instrumentation have drastically changed surgical approach, procedure and recovery. With these new procedures, i.e., endoscopy, arthroscopy, bronchoscopy, proctoscopy, etc., came the demand for new instrumentation appropriate for the procedure. One category of instruments is surgical retractors designed for the minimal approach usually required of surgical scope procedures and other minimal incision surgeries.

Those of ordinary skill in the art are familiar with the array of retractors used in their specialty. Many of these retractors are for highly specialized purposes and carry an eponym associated with its originator(s). For example, Senn, Seeburger, Holheimer, Weitlaner, Army-Navy and Hohmann are names associated with specific retractor types. These retractors, and countless others, have traditionally been used in what is referred to as "open surgery." Minimal incision surgery and surgical scope procedures in joints and body cavities require different types of retraction developed specifically for the procedure contemplated. Certain of those types of retractors exist. Examples of such retractors may be found in U.S. Pat. Nos. 5,558,665 and 5,888,196.

Body cavities, such as in the gastrointestinal tract, the stomach or the rectum, have been approached in an open surgical manner with a trans-abdominal incision for the stomach and a trans-perineum incision for the rectum. The anatomy of each area carries with it attendant complications in exposure and surgical time. A third technique, or category of techniques, in approaching an area of the GI tract is laparoscopy that use cameras and instruments introduced through small incisions. This technique can approach the gastrointestinal tract from the serosal rather than the luminal side of the hollow viscus. However, exposure here can be problematic as the entry into the hollow viscus would be through an enterotomy.

Surgery in each of these areas, and using any one of these or a number of other techniques, requires multiple layer dissection and retraction of vital structures. Some of the surgical approaches to different cavities carry problems common to each approach, including problems associated with minimal approaches used for surgical scope procedures. Endoscopic approaches for the rectum, such as a proctoscope, or for the stomach, such as a gastroscope, have common problems with exposure due to the anatomy and concomitant physiology of the area. Essentially, the incision for a surgical scope procedure is usually quite small in relation to the surgical field. To provide for adequate surgical working space and procedures, techniques have been developed to allow adequate exposure in the surgical field and, for the most part, minimize trauma and surgical time in the area. In one technique, the technique of insufflation, air is forced into the chosen body cavity, the peritoneum or bladder, for example, and can facilitate exposure and visualization. Alternatively, saline streams may be introduced into a body cavity to affect enhanced visualization.

The techniques of insufflation and hydrostatic pressure, although useful, are problematic in a number of ways. First, insufflation must be continuous. The problem is maintaining the balance of exposure versus continuous air pressure, which is necessary for insufflation. Continuous insufflation can produce new problems such as respiratory compromise and air leakage into surrounding tissues. Further, weaknesses in the walls of the surgical area may be further compromised by air or water pressure to the point of tearing, leading to increased bleeding, possibility of infection and prolonged healing time. Moreover, insufflation of air into the stomach or rectum can cause bowel dilatation in other parts of the gut, which is typically undesirable. The invention disclosed herein addresses certain of these problems in exposure during GI, alimentary, retroperitoneal, thoracic and other surgeries.

SUMMARY OF THE INVENTION

The invention is directed to surgical instrumentation which may be used in procedures directed to the alimentary canal, thoracic cavity or other areas of the body. A new surgical retractor is disclosed which provides for greater exposure during surgery while minimizing complications usually associated with similar surgeries performed using currently available retraction. Also contemplated in this invention is backside viewing of operative fields. To accomplish backside, or retrograde, viewing, a separate camera may be positioned at the distal area of the retraction and made to view proximally. A proximal camera may provide forward viewing, that view from superficial to deep, and a distal camera may provide backside viewing, that view from deep to superficial. Cameras viewing from different directions may provide better 3-D viewing of the surgical site. Novel access and visualization of body cavities not currently possible, such as inside the gut and in between muscle groups to reach long bone diaphysis and vessels, will be available to the surgeon.

The retractor's mechanism is made of light flexible wires that can be introduced through small passages or openings that exist in anchoring plates or channels along an endoscope. The extent of retraction is adjustable. The retractor mechanism, when expanded to the appropriate degree of retraction, can be locked in place and then unlocked and adjusted in position and expanded at the wish of the surgeon.

The expandable retractor expands from the distal point inside the anatomical space providing further room for surgical access and illumination. The retraction produced exists within the distal point and proximal point where the anchoring and guidance point may be locked and unlocked for adjustment. A distal or end receptacle may serve as the point of abutment or fixation for the retractor wires and the end point of a central rod. The distal receptacle may also serve as a point of articulation for operating instruments such as graspers and cutters, attachments for digital ultrasound, infrared spectrum instrumentation probes or any surgical instrument adapted for minimal incision surgery. In a preferred embodiment, the end receptacle is in fixed articulation to the distal end of the central rod. The distal point of retraction and illumination may be achieved by a fiber optic central rod, which nests in the end receptacle. The opening of the end receptacle faces the operator. The combination of the central rod and end receptacle may provide a backward source of light and a fixation point. Further, the receptacle acts as an articulation point for the flexible wires.

The number of retractor wires introduced may vary, according to the size and shape of the working space desired. Initially, a number of flexible wires may be in place within the expandable surgical retractor prior to entry into the surgical area. Following entrance into the surgical area, the surgeon, or operator may add additional flexible wires.

The bowing of the wires, fixed at two points, may provide the retraction, and the length of flexible wire introduced in between the two points of fixation determine the size of the bowing and space retracted. The flexible wires may be blunt at the distal end and carry a bulbous point to avoid injury to tissues and provide a simple fit in the end receptacle. Alternatively, the flexible wires may be fashioned so as to create an articulation with each other. The flexible wires are composed of any acceptable surgical material with the desired characteristics of strength, flexibility and compatibility with tissue. For example, stainless steel, inert plastics, and composites that are malleably, flexible and still strong enough to displace a desired piece of anatomy may be used. Flexible wires, as used herein, means any flexible material in any shape that may serve to retract structures. It is contemplated that differing shapes and durometer of materials can suffice for the flexible wires.

A third or fourth point of fixation may be slidably articulated or otherwise attached along the shaft of the central rod to keep wires aligned to allow working room along the introductory pathway from outside into the surgical retracted space. These points of articulation allow for easy movements of wire along the shaft and do not require a locking mechanism.

With respect to retrograde illumination and camera viewing, the source of illumination and camera viewing may be of unique importance since most surgical approaches thus far involve a forward viewing camera and source of light. Thus, the invention, in a preferred embodiment, may provide views heretofore too difficult or dangerous to the patient to pursue.

Due to the varying sizes contemplated for the expandable surgical retractor, the expandable surgical retractor may be removably attachable to a stand such as a self-supporting or freestanding stand.

DETAILED DESCRIPTION OF THE INVENTION

In a preferred embodiment of the invention, a central rod has a first end and a second end wherein the second end is articulating with an end receptacle. The end receptacle, in a preferred embodiment, is fixed to the second end. The central rod end may incorporate glass fibers for light and fiber optical capability. Anchoring plates may be slidably articulated or otherwise attached to the central rod and can be made to slide proximally and distally along the central rod. By slidably articulating with the central rod it is meant that the anchoring plates are not fixed to the central rod but may be made to slide along the length of the central rod. The site of articulation in the anchoring plates may be a central opening in the anchoring plate. The central rod is surrounded by a multiple of flexible wires. The flexible wires may be either solid or woven strand-type wires. The flexible wire is made from malleable and/or flexible material such as metals composites, surgical steel, inert plastics or combinations thereof. It is further contemplated that fiber optic material may be used for the flexible wires as well. It is understood that for the purposes of this invention, flexible wires may refer to any flexible material in any shape that may serve to retract structures. For example, the flexible wires may be metal strips of a certain width that provide additional pressure against anatomy so certain anatomy, the gut for example, does not push through into the surgical area retracted. It is contemplated that the central rod, at the discretion of the physician or other user, may be used as a handle while retraction is carried out via extension of a series of flexible wires, or that the central rod itself may be moved proximally and/or distally about the surgical site to expand and collapse flexible wires. It is further contemplated that the expandable surgical retractor may constructed to be removably attached to a stand to help support the expandable surgical retractor.

Figure 1:
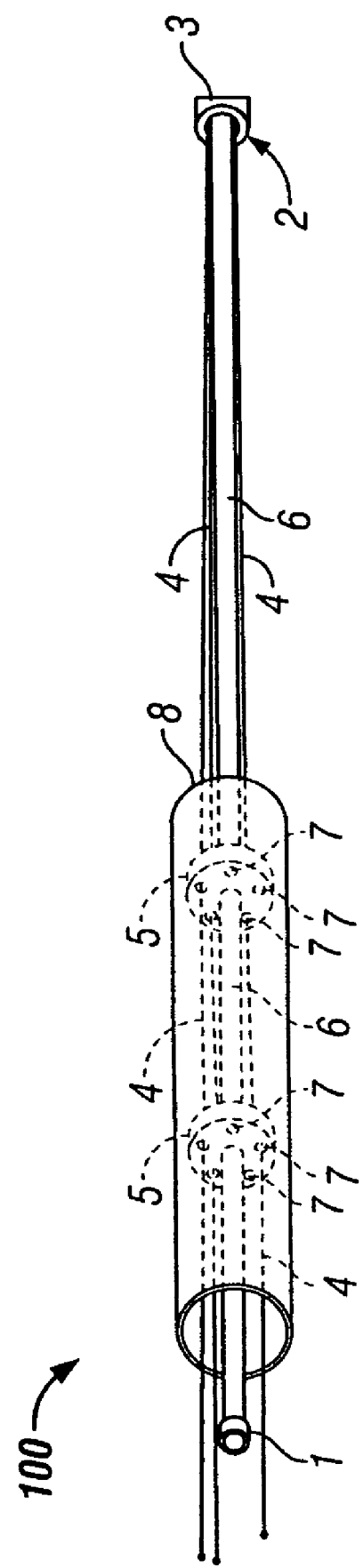
FIG. 1 depicts a lateral view of the expandable surgical retractor in a closed configuration.

Referring to FIG. 1, the expandable surgical retractor 100 has a first end 1 and a second end 2. The second end 2 contains the distal receptacle or end receptacle 3, which accepts the desired number of flexible wires 4. Situated between the distal receptacle 3 and first end are a multiple of fenestrated anchoring plates 5, plates with a number of openings, which may provide stability, guidance and anchoring for the flexible wires 4 and a fiber optic central rod 6. The anchoring plates 5 may be of any sturdy material that is compatible with tissue. The anchoring plates may be of a fiber optic material. Each of the anchoring plates 5 contains a plurality of passageways, or openings, 7 for passage of the flexible wires 4 and central rod 6. The central rod 6 may be made of fiber optic material allowing enhanced visualization about the retracted areas of tissue in the surgical field. A sheath 8 surrounds the anchoring plates. Not shown in the figure but contemplated in the invention are a third or fourth point of anchoring that can be slidably articulated along the shaft of the central rod to keep wires aligned to allow working room along the introductory pathway from outside into the surgical retracted space. These points of anchoring also contain openings for the flexible wires 4 and allow for easy movements of wires along the shaft and do not require a locking mechanism.

Figure 2:
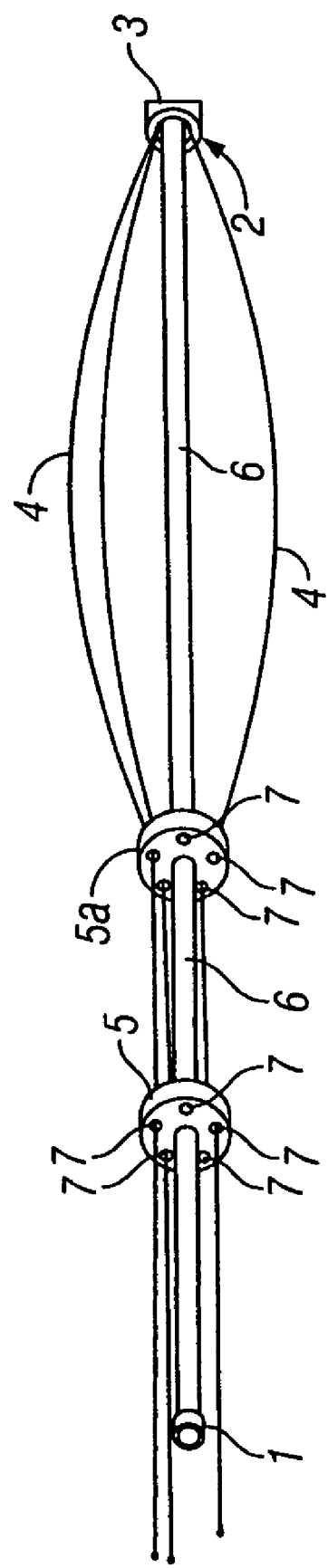
FIG. 2 depicts a lateral view of the expandable surgical retractor in an open or expanded configuration.
Figure 2A:
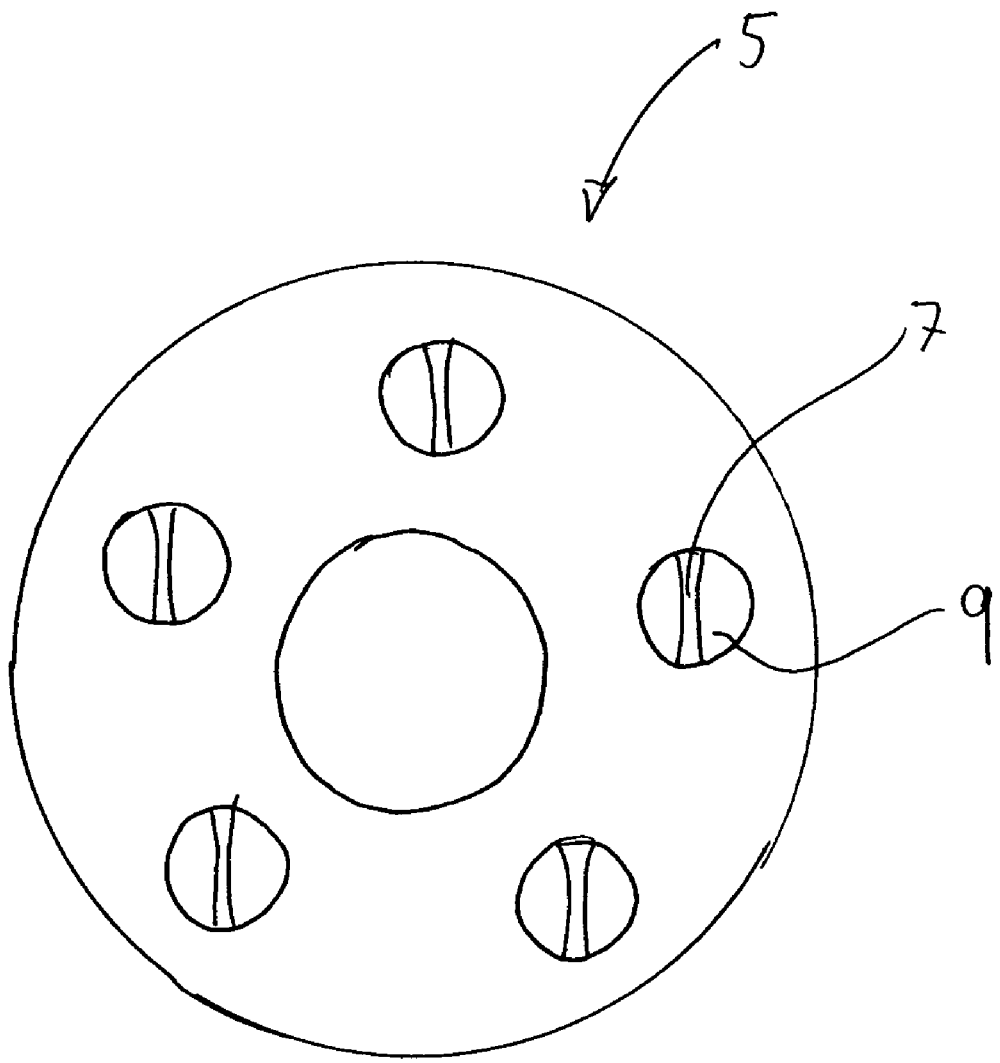
FIG. 2A depicts a magnified top view of an anchoring plate having a locking mechanism located in the openings on said plate.

FIG. 2 depicts the expandable surgical retractor in an open, or expanded, configuration. Similar to FIG. 1, the expandable surgical retractor has a first end 1 and a second end 2. The second end 2 contains the distal receptacle or end receptacle 3, which accepts the desired number of flexible wires 4. The distal receptacle may be designed with or without a locking mechanism. Situated between the distal receptacle 3 and first end are a multiple of fenestrated anchoring plates 5, plates with a number of openings, which provide stability, guidance and anchoring for the flexible wires 4 and a fiber optic central rod 6. Here, the flexible wires 4 have been locked to the anchoring plate 5, 5a with a locking mechanism 9 (shown in FIG. 2A) and the anchoring plates 5, 5a have been advanced distally (the surgeon being proximal), thereby providing a retrograde expansion of the flexible wires 4. As the anchoring plates 5, 5a are advanced distally; the moment of force is translated proximally from the area of greatest resistance, the end receptacle 3, to the first area of proximal flexibility, the flexible wires 4. The degree of retraction is thus in the control of the surgeon. Again, the central rod 6 may be made of fiber optic material allowing enhanced visualization about the retracted areas of tissue in the surgical field.

Referring to both FIGS. 1 and 2, a sheath, 8 surrounds the anchoring plates and a portion of the expandable surgical retractor proximal and distal to the anchoring plates 5, 5a. The sheath allows for unrestricted movement of the expandable portion of the expandable surgical retractor; excluding the rigid central rod. The sheath 8 protects the percutaneous entrance, movement and exit of the expandable surgical retractor and the associated surgical instruments. The flexible wires 4, at the distal ends, may be bulbous and blunt in shape in order to protect tissues that can abut against the wires during introduction to and removal from the expandable surgical retractor. Further, a blunt and spherical shape allows the best articulation within the distal receptacle 3.

The proximal anchoring point is the proximal anchoring plate 5a. Clustered in a ring configuration are openings 7 within the anchoring plate 5a to allow the expansion of the flexible wires in a geometrical, partial spherical, dome shaped space and allow desired spacing between the flexible wires 4. The openings within the anchoring plates 5, 5a, are lined with a material that allows smooth sliding of wires, such as Teflon®, a lubricant or other substance to decrease the coefficient of friction, and a clamping device for easy readjustment, fixation and sliding of wires. The anchoring plates contain a locking mechanism for the flexible wires. The locking mechanism may be selected from locking mechanisms known in the art. This group may include, but is not limited to, spring loaded clamping devices, pinch-slits in the anchoring plate wherein the slit is of a smaller area than the diameter of the flexible wire and the wire is then held in place when forced into the slit, threaded locking devices, wire shape conducive to hooking of the wire and external clamps. Additionally, a locking mechanism for the flexible wires 4 may also include a method of a hooking or threaded attachment sites in the distal receptacle 3.

For ease of positioning and placement of the flexible wires, the openings within the anchoring plates should have a very low coefficient of friction. For example, the openings may be lined with a material that allows smooth sliding of wires, such as Teflon® or other materials known in the art for decreasing friction or the abutting components may be composed of materials which are selected for, amongst other things, their coefficient of friction.

The dimensions of the expandable surgical retractor may be about 30 to 120 cm in length with the central rod being about 0.5 to 2 cm in diameter and the distal receptacle being about 1 to 3 cm in diameter and about 1 to 3 cm in depth. In a preferred embodiment, the length of the expandable surgical retractor may be about 60 cm, the diameter of the central rod may be about 1 cm and the end receptacle may be about 2 cm in depth and 2.5 cm in diameter. The diameter of the anchoring plates may be variable depending upon the rigidity sought in the expandable surgical retractor and the type of locking mechanism chosen for the flexible wires. For example, the diameter of the anchoring plates may be dependent on the area of the anatomy visualized. It is further contemplated that the anchoring plates may be adjustable as to diameter without the necessity of changing the anchoring plate. For example, the anchoring plates may be fashioned to be expandable and collapsible via rotation about the central rod.

The anchoring plates for viewing structures within muscle compartments may be of less diameter than anchoring plates used in the peritoneal cavity. Intra-alimentary spaces differ in size by virtue of natural anatomy, genetics and pathology. It is contemplated that a number anchoring plates of differing diameter will be available to the surgeon during any one procedure. For example, anchoring plates may be available in 0.5 cm increments, i.e., 0.5. 1.0, 1.5 cm, etc. Anchoring plates, at a minimum, should be supplied in pairs where each in a pair have an equal diameter. If, in one case, retraction were needed within the sigmoid, descending and transverse colon, differing degrees of retraction may be facilitated by using different size anchoring plates.

The end receptacle may serve as an articulation point for surgical instrumentation such as cutters, forceps, probes or the like, and diagnostic modalities such as digital ultrasound, infrared spectrum instrumentation, cardiovascular wires or the like.

In another embodiment of the invention, a more rigid endoscope is contemplated. The flexible wires, which are of a greater duometer for increased strength, may pass through specific a plurality of openings in the wall of the endoscope. The wires may be directed through the plurality of openings accommodating the caliber of the wires and allow smooth advancement and retraction of the wires in the wall of the endoscope. The wires, once advanced, form a loop at the end of the scope. For example, for use as a rectal endoscope, three looped wires forming half a spherical circumference each may be placed equidistantly in the tube shaft of the scope; thus six total channels, with three wires. Once the scope is placed in the rectum, and the pathology is in view, the wires may be pushed out into the lumen forming a loop with a larger diameter, pushing out the wall of the rectum and providing adequate room and exposure around the designated site and lesion, i.e. a polyp. The wire loops cross approximately in the center and distal part of the loop. The length of the wires advanced or retracted can be adjusted according to the length or the diameter of the loop desired.

In the rigid endoscope embodiment of the invention, the expandable surgical retractor may function in the gut spaces just inside the outside surface, as in the rectum, mouth, peritoneal and thoracic space. For the peritoneal and thoracic space, a small incision in the abdominal or thoracic wall will be required to insert the endoscope with the retraction mechanism.

The instant retraction mechanism adds advantages over current retractors in that the flexible wires offer a more forgiving and malleable retraction than angled plates, or arms, as are disclosed in U.S. Pat. No. 5,888,196. A further advantage over existing retraction devices is the removable nature of the flexible wires in the instant invention. Further, expansion may be controlled and occurs at the distal end of the retractor. The disclosed retractor may also function by creating an empty lumen to work within as well as offering removable wires.

In another embodiment of the invention, the central rod does not extend beyond the distal anchoring plate. In this embodiment, the flexible wires may contain a functional articulation point at their distal end. It is contemplated that each functional articulation point of each flexible wire at its distal end will be so formed to meet and lock with a mating flexible wire. For example, a ball and socket arrangement may be used wherein on flexible wire contains a socket at its distal end to meet with a mating flexible wire which contains a ball at its distal end. Other articulation mechanisms may be used such as threaded members, hooks, and friction fits. Once the mating flexible wires are articulated distally, the surgeon may exert a force proximally that is directed through the mating flexible wires to the distal articulation point, therein forcing the mating flexible wires to arc away from each other. This arcing of the mating flexible wires will thus create an ellipsoid or circular shape about the mating flexible wires. In this embodiment, specifically shaped areas of retraction may be possible by locking the mating flexible wires at the anchoring plates in differing degrees of extension. Thus, it may be possible to specifically retract certain structures while avoiding other structures altogether, a weakened artery for example.

Further, in this aspect of the invention, it is contemplated that the functional distal articulation point of the flexible wires, when articulated, will form a distal cup for use in retrograde illumination and viewing. The cup will be formed by the configuration of the ends of the flexible wires when the flexible wires are articulated.

In another embodiment of the invention, the central rod does not extend beyond the distal anchoring plate and the flexible wires are guided through individual sleeves about a rigid central rod. In this embodiment, the flexible wires are introduced at the proximal end of the sleeve and made to exit at the distal end of the sleeve. The flexible wires may be preformed for shape or may be straight. Flexible wires in this embodiment will contain a functional distal articulation point at its distal end. Each flexible wire may then meet an appropriate mating wire via the distal articulation. For example, the distal articulation point may be a ball and socket articulation wherein the ball exists at the distal end of one wire while the socket exits at the distal end of a mating wire. Other articulation mechanisms may include threaded members, hooks and friction fits. Preformed wires may be used to facilitate the meeting of appropriate wires.

Further, in this aspect of the invention, it is contemplated that the functional distal articulation point of the flexible wires, when articulated, will form a distal cup for use in retrograde illumination and viewing. The distal cup will be formed by the configuration of the ends of the flexible wires when the flexible wires are articulated.

In another embodiment of the invention, a flexible deployment tube is used with the expandable surgical retractor. In this embodiment of the invention, the central rod is flexible. The introduction of the device may be through a flexible plastic tube that can be introduced over 40-60 cm to reach spaces further away from the surgeon's hands, such as the stomach, operating from and through the mouth, or deep inside the peritoneal cavity in a large individual. A suitable fiber optic material for the central rod is contemplated here as well.

The retractor mechanism may function in a way similar to the rigid endoscope embodiment and the wires may also expand in spherical manner from a collapsed cylindrical shape. To accomplish this spherical expansion, multiple long interconnected wires may be deployed by a pulling or pushing mechanism on the central shaft and the combination of wires will self-expand in a geodesic shape. The entire mechanism can fit into a sheath, 5-8 mm in diameter, that is flexible and blunt ended and may be passed through the mouth, through the esophagus and into the stomach. When expanded, the retractor provides a spherical, disc or domed shaped space that may be 5-10 cm in size. The flexible device may also be introduced into the peritoneal cavity and retroperitoneal space and provide exposure in areas not favorable to insufflation or hydrostatic pressure. Further, flexible wires can allow bending around corners and solid structures or visceral organs such as the liver.

It is also contemplated that the expandable surgical retractor may be supplied in a kit containing the various parts. The kit may contain the positioning device, flexible or rigid, for a plurality of wires. The positioning device may comprise the central rod in any of its variations, the handle in any of its variations, or other suitable positioning device for the flexible wires. The kit may also contain any of the flexible wires or materials with an end receptacle for various embodiments described herein, light source and anchoring plates. In this kit, the central rod, handle, or other device for positioning the wires may be referred to as a positioning device. Thus, the flexible wires selected for the kit will accommodate the type of positioning device selected. For example, a handle for a rectoscope may be supplied in a kit wherein the flexible wires are those designed for an entry through one of the plurality of openings and exit through a separate one of the plurality of openings. Thus forming a looping type end as described above. Additionally, the flexible wires may contain the necessary design to create a distal articulation point to form a distal cup, also as described above.

The anchoring plates may be supplied in multiples of two so that at least two anchoring plates will be similar in diameter. Thus, at least two anchoring plates will have a diameter of 0.5 cm, 1.0 cm, 1.5 cm and so on. In a preferred embodiment of this kit, the parts of the expandable surgical retractor may be composed of disposable materials such as plastics. The kit will also contain instructions for use of the expandable surgical retractor.

Figure 3:
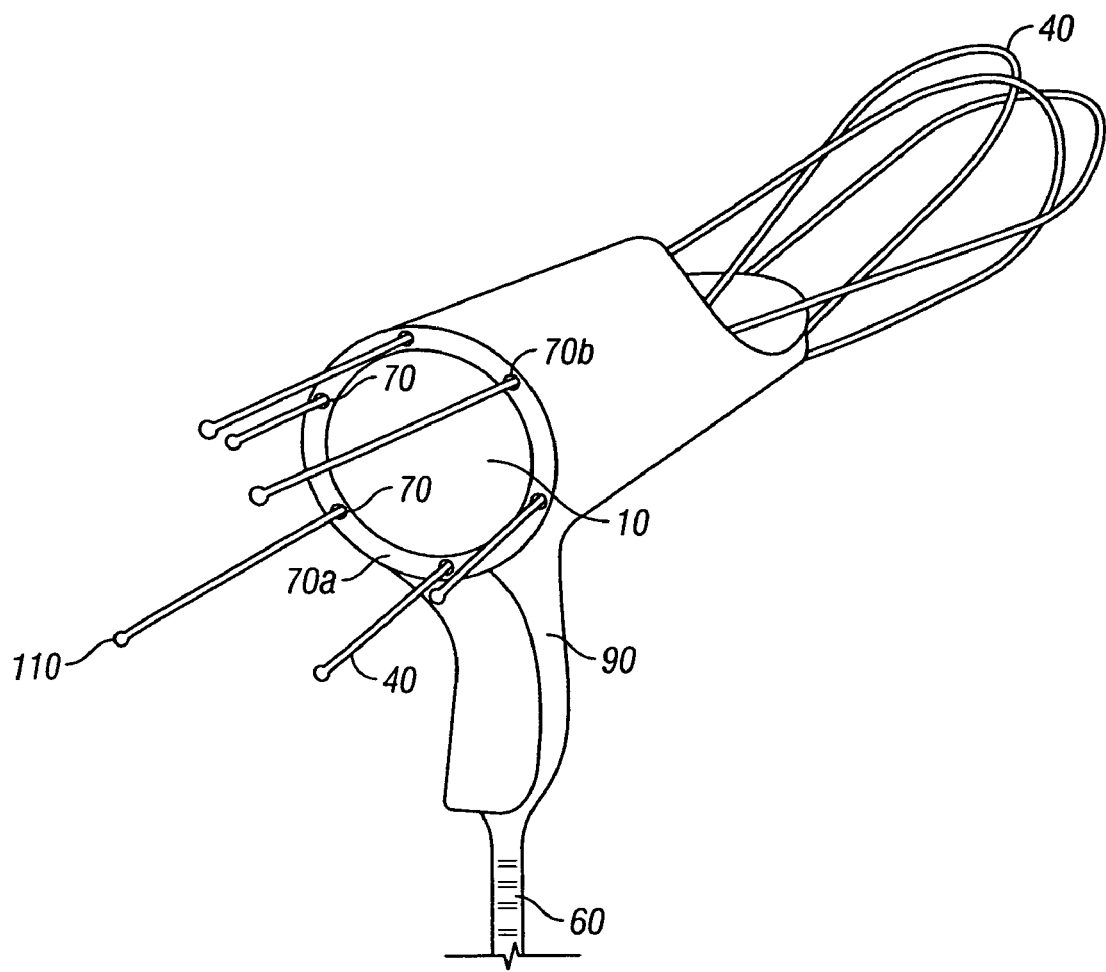
FIG. 3 depicts an additional embodiment of the expandable surgical retractor in which the central rod has been replaced by an aperture in a handle. The aperture is surrounded by flexible wires.

In another embodiment of the invention, depicted in FIG. 3, a handle 90 with an aperture 10 replaces the central rod. The handle contains an attachment for, or its own, light source 60 which may direct light into the aperture 10 and proximal and distal to the aperture. Thus, the light source may be permanently attached to the handle or may be a temporary light source made to attach to the handle.

The handle 90 may be shaped in such a way so as to conform the planned procedure. For example, in FIG. 3, a design contemplated for retraction and proctoscopy is disclosed. Alternative shapes may be used, such as colposcopy, where the handle if adapted for the cavity scoped. Thus the handle may be adapted to any selected area of anatomy where retraction is contemplated.

Similar to the rigid endoscope embodiment of the invention, this embodiment may use flexible wires of increased durometer. In this embodiment, it is contemplated that the flexible wires, 40 will fit into openings 70 which subtend a circular configuration in the handle 90. At the inferior portion of the handle is an attachment for a light source 60. The flexible wires 70 may be pre-installed into the openings 70 of the aperture 10 and each flexible wire 70 may contain a bulbous end 110 on each end of the wire to maintain the wire within the openings of the aperture. The flexible wires 70 may enter one opening 70a and exit a separate opening 70b on the same aperture. The retraction is maintained by the fit of multiple flexible wires in the aperture 10. The amount of retraction is controlled by the surgeon or the surgeon's assistant by pushing or pulling on the wires. When the flexible wires 70 of this embodiment are extended the distal aspect of the expandable surgical retractor may look somewhat like a whisk type eggbeater.

It is also contemplated that this embodiment of the invention may contain a handle 90 which is made of a transparent material. Similar to all embodiments described herein, it is contemplated that the aperture will allow surgical instrumentation, cameras, ultrasound, probes, catheters, infrared spectrum instruments or the like to be used with enhanced visualization at the surgical site. Further, the flexible wires may be in communication with the handle only and then articulate with each other distally. The flexible wires can be pre-stressed to curve in an "out then in" fashion as they emerge from the handles. Alternatively, the retrograde forces of the selected anatomy. The flexible wires may also be shaped via internal forces similar to the way that flexible endoscopes or catheter placement devices, can be curved inside lumens or vessels. These internal forces may be created mechanical, pneumatic or hydraulic forces. In this way, the flexible wires of this embodiment may be controllably deformed distal to their emergence from the handle. As with the embodiments disclosed herein, it is contemplated that the flexible wires will meet distally to form a point upon which further expansion of the wires may be achieved. Additionally, the meeting of the distal wires may form a placement point for a procedural or diagnostic medical device.

In each of the embodiments described herein, it is further contemplated that a stand for the expandable surgical retractor may be used. This stand can either be a stand-alone device at the side of the operating table, one in which the expandable surgical retractor is supported by the stand standing on the floor. Another type of stand is contemplated wherein the expandable surgical retractor is supported by a stand that mounts to the operating table. By using a stand for the expandable surgical retractor the surgeon maintains better control over the retractor and has better access to the flexible wires.

It is also contemplated that in each embodiment of the expandable surgical retractor, surgical reparative surgical instrumentation and diagnostic instrumentation can be used with the expandable surgical retractor. This instrumentation may include but is not limited to, surgical scopes, infrared spectrum instruments, ultrasound, cardiovascular wires, stent deployment modalities, catheters, cutters, burs, scalpels, curettes, forceps, electrical or pneumatic surgical instruments and prosthetic deployment modalities. It is further contemplated that the expandable surgical retractor may be supported by a self-supporting stand which is connected to the operating table or other stable structure to facilitate manipulation of the retractor by the inventor.

EXAMPLE I

Application of a Preferred Embodiment

Numerous applications for a preferred embodiment of the invention are available. For example, a surgeon may obtain enhanced visibility in anatomical spaces in the peritoneal cavity, such as in the lateral gutter against colon or infra diaphragmatic space for work around the spleen; around and inside the gut and bladder; tissue spaces within the abdominal wall, such as for repair of inguinal hernias; in between muscle groups such as between the quadriceps and femur; and neurovascular channels such as Hunter's canal.

In this example, the intraluminal gut space is approached through the abdominal wall by making a small enterotomy to enter the inside of the gut. (As mentioned above, a transluminal approach would be through the anus or mouth.) The expandable surgical retractor may be introduced into the surgical field through the incision, which may be made using a trocar or scalpel or other incision technique known in the art. The fiber optic rod 6 has previously been placed within the sheath 8 with the anchoring plates 5, 5a. Attention may be directed to the surgical field where the distal or second end 2 of the expandable surgical retractor is at or within the surgical field. The fiber optic central rod 6 may provide illumination for forward and backward visualization.

Retraction may be achieved by placing the flexible wires 4 into the passageways, openings, 7 of the anchoring plates 5, 5a and extending the flexible wires 4 to the distal receptacle 3. For ease during surgery, a certain number of flexible wires 4 may be installed in the expandable surgical retractor prior to introduction of the expandable surgical retractor into the surgical site. Non-traumatic retraction may be produced by placing an anterograde moment of force on the flexible wires 4. The anterograde force is reflected by the distal receptacle 3 in retrograde moment to effect a semicircular configuration in the flexible wires 4 expanding the flexible wires within the surgical field and providing for visualization.

An advantage of this type of retraction may exist in the flexible wire's ability to deform relative to structures with greater stability, bones and certain fasciae including the transverse abdominis aponeurosis and the lumbodorsal fascia. Further, as there are calculated spaces between the flexible wires 4, procedures may be performed with instrumentation appropriate for the space created by the expandable surgical retractor. Upon visualization of the pathology, the appropriate instrumentation may be delivered to the surgical field while using the expandable surgical retractor.

EXAMPLE II

Advantages of the Expandable Surgical Retractor in Intrathoracic Procedures

Additional advantages exist with use of the expandable surgical retractor in other anatomic regions of the body. Intrathoracic surgery is one example. The intrathoracic cavity has been the focus of past and current technologies developed to allow surgical scope procedures in the thorax. Current retraction is commonly provided by the above described insufflation techniques. A major disadvantage of insufflation in the intrathoracic space is the depressed ventilation forced upon the ipsilateral or contralateral lung. In other words, the lung opposite the surgical site cannot inflate.

Further, unidentified weaknesses in the lung parenchyma, blebs for example, may rupture during insufflation and could lead to artificial pneumothorax and/or extrapleural pneumothorax, the sequelae of which may be devastating. Use of the expandable surgical retractor as described avoids the necessity of continuous insufflation in the intrathoracic space and presents a forgiving surgical retractor in relation to non-deforming or lesser deforming tissues. Moreover, the possibility of external pressure against the pericardium is eliminated. This is especially important where cardiac tampanode may be an issue.

From the foregoing, it will be appreciated that specific embodiments of the invention have been described herein for purposes of illustration, but that various modifications may be made without deviating from the spirit and scope of the invention. Accordingly, the invention is not limited except as by the appended claims. The preceding Examples are intended only as examples and are not intended to limit the invention. It is understood that modifying the examples above does not depart from the spirit of the invention. It is further understood that the each example may be applied on its own or in combination with other examples.

The invention claimed is:

1. An expandable surgical retractor comprising:
a central rod with a first end and a second end;
an end receptacle that articulates with the second end;
a plurality of anchoring plates slidably articulated to the central rod wherein each anchoring plate contains a plurality of openings;
a plurality of flexible wires each with a proximal end and a distal end which may be placed in the plurality of openings; and
a locking mechanism at each opening in the plurality of openings.

2. The expandable surgical retractor of claim 1, wherein the flexible wires may be selectively introduced into the openings of the anchoring plates and end receptacle.

3. The expandable surgical retractor of claim 1, wherein a central opening for articulation with the central rod is situated at the epicenter of the plurality of openings.

4. The expandable surgical retractor of claim 3, wherein the central opening has a diameter larger than a diameter of the central rod.

5. The expandable surgical retractor of claim 3, wherein the openings in the plurality of surrounding openings have a diameter larger than a diameter of the flexible wires.

6. The expandable surgical retractor of claim 1, wherein the central rod slidably articulates with the anchoring plates through the central opening.

7. The expandable surgical retractor of claim 1 wherein the anchoring plates, central rod, flexible wires and/or the end receptacle are composed of fiber optic material.

8. The expandable surgical retractor of claim 1, wherein the locking mechanism may be selected from the group consisting pinch slits, threaded locking devices, loops, hooks, clamps and wire shape.

9. The expandable surgical retractor of claim 8, wherein the locking mechanism may be located in the anchoring plate, the end receptacle or both.

10. The expandable surgical retractor of claim 1 wherein the central rod is solid.

11. The expandable surgical retractor of claim 1 wherein the central rod is hollow.

12. The expandable surgical retractor of claim 1 wherein the expandable surgical retractor is removably attachable to a stand.

13. An expandable surgical retractor comprising:
a fiber optic central rod with a first end and a second end;
an end receptacle that articulates with the second end;
a plurality of anchoring plates slidably articulated to the central rod wherein each anchoring plate contains a plurality of openings;
a plurality of flexible wires each with a proximal end and a distal end which may be placed in the plurality of openings; and
a locking mechanism at each opening in the plurality of openings.

14. The expandable surgical retractor of claim 13, wherein the flexible wires may be selectively introduced one by one into openings of the anchoring plates and end receptacle.

15. The expandable surgical retractor of claim 13 wherein the anchoring plates, flexible wires and/or the end receptacle are made of fiber optic material.

16. The expandable surgical retractor of claim 13, wherein a central opening for articulation with the central rod is situated at the epicenter of the plurality of openings.

17. The expandable surgical retractor of claim 13, wherein the central rod slidably articulates with the anchoring plates via the central opening.

18. The expandable surgical retractor of claim 17, wherein the central opening has a diameter larger than a diameter of the central rod.

19. The expandable surgical retractor of claim 18 wherein the openings in the plurality of surrounding openings have a diameter larger than a diameter of the flexible wires.

20. The expandable surgical retractor of claim 13, wherein the locking mechanism may be selected from the group consisting of pinch slits, threaded locking devices, loops, hooks, clamps and wire shape.

21. The expandable surgical retractor of claim 13, wherein the locking mechanism may be located in the anchoring plate, the end receptacle or both.

22. The expandable surgical retractor of claim 13 wherein the central rod is solid.

23. The expandable surgical retractor of claim 13 wherein the central rod is hollow.

24. The expandable surgical retractor of claim 13 wherein the expandable surgical retractor is removably attachable to a stand.

25. An expandable surgical retractor kit containing:
a positioning device for a plurality of flexible wires;
a plurality of anchoring plates slidably articulated to a central rod each of which contains a central opening surrounded by a plurality of openings;
a plurality of flexible wires each with a proximal end and a distal end;
a locking mechanism for the flexible wires for each opening in the plurality of openings; and
instructions for assembly and use.

26. The kit of claim 25, wherein the plurality of anchoring plates, plurality of flexible wires, the central rod and/or an end receptacle are made of fiber optic material.

27. The kit of claim 25, wherein the plurality of anchoring plates are supplied in multiples of two where at least two anchoring plates within the multiple of anchoring plates have equal diameter.

28. The kit of claim 25 wherein the anchoring plates range in diameter from 0.5 cm to 10 cm in increments of 0.5 cm.

29. The kit of claim 25, wherein the central rod with an end receptacle, multiple of anchoring plates and flexible wires are made of disposable material.

30. The kit of claim 25, wherein the locking mechanism may be selected from the group consisting of pinch slits, threaded locking devices, loops, hooks, clamps and wire shape.

31. The kit of claim 25 wherein the positioning device for a plurality of wires is removably attachable to a stand.

32. An expandable surgical retractor comprising:
a central rod with a first end and a second end;
a plurality of anchoring plates slidably articulated to the central rod wherein each anchoring plate contains a central opening surrounded by a plurality of openings;
a distal anchoring plate which articulates with the second end of the central rod;
a plurality of flexible wires each with a proximal end and a distal end which may be placed in the plurality of openings;
a functional articulation point at the distal end of the flexible wires; and a locking mechanism at each opening in the plurality of openings.

33. The expandable surgical retractor of claim 32, wherein the flexible wires may be selectively introduced into the openings of the anchoring plates.

34. The expandable surgical retractor of claim 32, wherein a central opening for articulation with the central rod is situated at the epicenter of the plurality of openings.

35. The expandable surgical retractor of claim 32, wherein the central rod slidably articulates with the anchoring plates through the central opening.

36. The expandable surgical retractor of claim 32 wherein the central rod and flexible wires are composed of fiber optic material.

37. The expandable surgical retractor of claim 32, wherein the central opening has a diameter larger than a diameter of the central rod.

38. The expandable surgical retractor of claim 32, wherein the openings in the plurality of surrounding openings have a diameter larger than a diameter of the flexible wires.

39. The flexible wires of claim 32 wherein the functional articulation point is a point for a meeting and articulation of two or more flexible wires.

40. The flexible wires of claim 39 wherein the meeting and articulation of two or more flexible wires creates a cup formation.

41. The expandable surgical retractor of claim 32, wherein the locking mechanism may be selected from the group consisting pinch slits, threaded locking devices, loops, hooks, clamps and wire shape.

42. The expandable surgical retractor of claim 32 wherein the central rod is solid.

43. The expandable surgical retractor of claim 32 wherein the central rod is hollow.

44. The expandable surgical retractor of claim 32 wherein the expandable surgical retractor is removably attachable to a stand.

45. An expandable surgical retractor comprising:
a handle with an aperture, wherein the handle further comprises a light source;
a plurality of openings surrounding the aperture;
a plurality of flexible wires which fit in the openings surrounding the aperture; wherein the flexible wires contain a bulbous end on each end of the wires to maintain the wires within said openings.

46. The expandable surgical retractor of claim 45 wherein the flexible wires enter one opening of the aperture and exit a separate opening of the aperture.

47. The expandable surgical retractor of claim 45 wherein the flexible wires enter and exit only one opening of the aperture.

48. The expandable surgical retractor of claim 45 wherein the handle may be adapted to fit a selected area of anatomy.

49. The expandable surgical retractor of claim 45 wherein the handle may be removably attached to a stand.

50. An expandable surgical retractor kit containing:
a positioning device for a plurality of flexible wires;
a plurality of anchoring plates each of which contains a central opening surrounded by a plurality of openings wherein the plurality of anchoring plates are supplied in multiples of two where at least two anchoring plates within the multiple of anchoring plates have substantially equal diameter;
a plurality of flexible wires each with a proximal end and a distal end;
a locking mechanism for the flexible wires for each opening in the plurality of openings; and
instructions for assembly and use.

51. An expandable surgical retractor comprising:
a central rod with a first end and a second end;
an end receptacle that articulates with the second end;
a plurality of anchoring plates slidably articulated to the central rod wherein each anchoring plate contains a plurality of openings and wherein the plurality of anchoring plates are supplied in multiples of two where at least two anchoring plates within the multiple of anchoring plates have substantially equal diameter;
a plurality of flexible wires each with a proximal end and a distal end which may be placed in the plurality of openings; and
a locking mechanism at each opening in the plurality of openings.

* * * * *